United States Patent [19]

Nakagawa et al.

[11] Patent Number: 5,248,676
[45] Date of Patent: Sep. 28, 1993

[54] ESTRADIOL PERCUTANEOUS ADMINISTRATION PREPARATIONS

[75] Inventors: Akira Nakagawa; Munehiko Hirano; Miyuki Shinmura, all of Tosu, Japan

[73] Assignee: Hisamitsu Pharmaceutical Co., Inc., Saga, Japan

[21] Appl. No.: 834,335

[22] PCT Filed: Apr. 26, 1991

[86] PCT No.: PCT/JP91/00578
§ 371 Date: Mar. 9, 1992
§ 102(e) Date: Mar. 9, 1992

[87] PCT Pub. No.: WO91/11752
PCT Pub. Date: Nov. 28, 1991

[30] Foreign Application Priority Data

May 17, 1990 [JP] Japan ................. 2-128160

[51] Int. Cl.$^5$ ............................................. A61K 31/56
[52] U.S. Cl. ................................... 514/182; 424/449; 514/947
[58] Field of Search ............................. 514/182

[56] References Cited

U.S. PATENT DOCUMENTS 4,994,267 2/1991 Sablotsky ..................... 514/182

FOREIGN PATENT DOCUMENTS 0156565 10/1985 European Pat. Off. .
0186019 7/1986 European Pat. Off. .
0341202 11/1989 European Pat. Off. .
0452837 10/1991 European Pat. Off. .
2045618 11/1980 United Kingdom .

OTHER PUBLICATIONS

Serveur Eqoque & File Japs, & JP-A-60 188-314 (Yamanouchi Seitaku K.K.) Sep. 25, 1985—Whole Abstract.
STN File Server, File CA & Chemical Abstracts, vol. 113, No. 8, abstract No. 65348r. Columbus Ohio U.S.; and JP-A-01 297,069 (Hisamitsu Pharmaceutical Co., Inc.) Nov. 30, 1989–whole abstract.

*Primary Examiner*—Leonard Schenkman
*Attorney, Agent, or Firm*—Bucknam and Archer

[57] ABSTRACT

1. An estradiol percutaneous administration preparation comprising:
(1) a (A—B) nX or (A—B) n—A type elastomer wherein A is substantially monovinyl-substituted aromatic compound polymer block, B is substantially a conjugated diolefin copolymer block, n is an integer of 3–7, and X is a residue derived from a polyfunctional compound combined with n of polymer chain (A—B),
(2) crotamiton and
(3) a super absorbent polymer, the preparation further comprising estradiol as the medicinal ingredient and exhibiting sufficient medicinal efficacy without causing rubefaction, rashes and the like.

5 Claims, 3 Drawing Sheets

ESTRADIOL PERCUTANEOUS ADMINISTRATION PREPARATIONS

TECHNICAL FIELD

This invention relates to an estradiol percutaneous administration preparation suitable for durably releasing estradiol therefrom.

PRIOR ART

Estradiol is estrogen (follicle hormone) secreted from the ovary of a woman during her reproducible period of time. Thus, women who are at the menopause or thereabouts become lacking in estradiol whereupon they suffer from their menopausal disorder, irregular menstruation or the like. Remedies for these symtoms are now made by the use of orally administrable preparations, but these preparations are rapidly metabolized by digestive canals such as stomachs and intestines, and livers so that they become inactive. Thus, in order to obtain sufficient medicinal efficacy, a large dose of estradiol must be administered. The use of such a high dose is very likely to cause adverse reactions and the like.

Therefore, some publications indicate that the percutaneous administration of preparations without passage through digestive canals and the liver has been studied. They include, for example, Japanese Pat. Appln. Laid-Open Gazette No. Sho 57-154122 or No. 154122/82 which discloses a method for controlling the release of estradiol dissolved in a hydroxypropylcellulose-ethanol gel through an ethylene-vinyl acetate membrane, Japanese Pat. Appln. Laid-Open Gazette No. Sho 60-152413 or No. 152413/85 which discloses only a menthol-containing percutaneous absorption preparation as a percutaneous absorption accelerator but is silent about pasting agents, Japanese Pat. Appln. Laid-Open No. Sho 61-17513 or No. 17513/86 which discloses a medicinal composition using therein a medicine permeation accelerator obtained by mixing propylene glycol with glycerine in a specified ratio, Japanese Pat. Appln. Laid-Open Gazette No. Sho 61-155321 or No. 155321/86 discloses a tackifier base containing as the principal ingredient a polymer capable of swelling in water, the polymer being illustrated by, as a tackifier base, tacky resin materials (polyterpene resins, hydrocarbon resins, etc.), natural or synthetic rubber (polyisobutylene, styrene-butylene polymers, styrene-isoprene polymers, styrene-ethylene-butylene polymers, 1,4-polyisoprene, etc.), galactmonnane, etc., and Japanese Pat. Appln. Laid-Open Gazette No. Sho 63-233916 or 233916/88 which discloses a pasting agent relative to a device composed of 7-layer laminated body.

The estradiol percutaneous administration preparations under various studies as mentioned above need specified processes in the production of the preparations because of their complicated structure and the like and therefore need an expensive apparatus to produce them. Further, the preparations are low in biological utility since the active materials contained therein can be used only to a limited extent. In addition, the addition of absorption accelerators such as ethanol will raise a problem as to skin stimulation from the standpoint of percutaneous administration.

In view of the above disadvantages, the present inventors made intensive studies in attempts to provide estradiol percutaneous administration preparations which have a simple structure, improved biological utility and lower skin stimulation and, as the result of their studies, they accomplished the present invention.

Disclosure of the Present Invention

The estradiol percutaneous administration preparation of the present invention comprises as the base:

1) (A−B) nX or (A−B) n−A type elastomer (elastic polymer) wherein A is substantially a monovinyl-substituted aromatic compound polymer block, B is substantially a conjugated diolefin copolymer block, n is an integer of 3-7, and X is a residue derived from a polyfunctional compound and combined with n of polymer chain (A−B), 2) crotamiton and 3) a super absorbent polymer and further comprises estradiol as the medicinal ingredient.

Estradiol used in the present invention is generally called estra-1. 3. 5 (10) trienne-3.17β-diol and is represented by the following structural formula

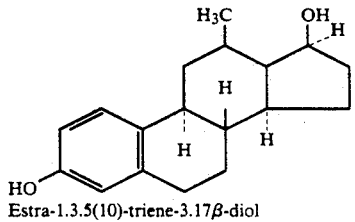

Estra-1.3.5(10)-triene-3.17β-diol

The percutaneous administration preparations of the present invention contain estradiol in an amount by weight of 0.01-10%, preferably 0.05-5% and more preferably 0.1-1%.

The (A−B) nX or (A−B) n−A type elastomers used as the base in said preparations are those which are commercially easily available, and they include a styrene-butadiene-styrene block copolymer (Califlex TR-1101 produced by Shell Chemical Corp.), a styrene-isoprene-styrene block copolymer (Califlex TR-1107, —1111 produced by Shell Chemical Corp.), Solprene 418 produced by Philip Petroleum Co., JSR 5000 produced by Nippon Synthetic Rubber Co., and Quintack 3421 produced by Nippon Zeon Co. with the styrene-isoprene-styrene block copolymer being particularly preferred. the use of the (A−B) nX or (A−B) n−A type elastomer as the base for the preparations will enable the releasability of estradiol from the preparations and the biological utilizability of the estradiol to be greatly enhanced.

Crotamiton used in the present invention is superior in dissolving estradiol thereby to widely improve the releasability and percutaneous absorption of estradiol from the preparations. Further, crotamiton had never been incorporated as a solubilizer and absorption accelerator for estradiol before the accomplishment of the present invention and there is found no literature which suggests the above incorporation.

The super absorbent polymer in an amount at least 10 times the weight of said high molecular material itself in order to be gelled and swollen. Such materials are preferably in the fine powder form and they include, for example, polyacrylic acid and metal salts (such as sodium salt) thereof; carboxymethylated polyvinyl alcohols, carboxy-methylcellulose and metal salts thereof; carboxymethyl polymers into which slight cross-linking bondage has been introduced; and starch acrylonitrile graft saponification metal salts. Fine powders of the above compounds are particularly preferably used.

The super absorbent polymers are illustrated by Sanwet (IM-300, IM-1000, IM-10000MPS, etc. produced by Sanyo Kasei Co., Japan), Aquakeep which is starch-grafted polyacrylate (4S, 4SH, etc. produced by Seitetsu Kagaku Co.), Sumikagel which is a polyacrylic acid and metal salt thereof (SP-520, SP-540, N-100, NP-1020, NP-1040, etc. produced by Sumitomo Chemical Co. which is acrylic acid-vinyl alcohol copolymer) and Arasorb (800, 800FS-100F, etc. produced by Arakawa Chemical Co. which is polyacrylic acid and its metal salts).

The use, in the preparation, of the base containing as the essential components the elastomer, crotamiton and super absorbent polymer will enable the preparation to improve the utility of estradiol and to widely lessen not only the degree of stuffiness caused by perspiration or the like on a skin portion to which the preparation is applied but also rubefaction and rash caused by medicinal stimulus.

The preparation of the present invention preferably contains the (A−B) nX or (A−B) n−A type elastomer, crotamiton and super absorbent polymer in the following respective proportions.

The total amount of the above elastomer, crotomiton and super absorbent polymer is preferably 20-99% and more preferably 30-60% by weight of the preparation. The amount of the (A−B) nX or (A−B) n−A type elastomer contained in the preparation is preferably 5-50% and more preferably 10-30%, by weight thereof, the amount of crotamiton is preferably 1-20% and more preferably 2-10% by weight of the preparation, and the amount of the super absorbent polymer is preferably 1-20% and more preferably 2-10% by weight of the preparation. A combination of these ingredients in the above specified amounts with estradiol in the previous specified amount will exhibit the effect or advantage of the present invention most remarkably.

The estradiol percutaneous administration preparation of the present invention may, in addition to the essential components, be incorporated with hitherto known ingredients asn antioxidant, a softening agent (for example, liquid paraffin), a tack-providing agent, an inorganic filler, an anti-aging agent and the like, each in a suitable amount, as required.

Backing materials for the preparations of the present invention are desirably those which have no effects on the release of medicinal substances and are superior in flexibility, and they preferably include polyester films, polypropylene films, polyethylene films, aluminum foils and flexible laminates thereof; laminates of polyvinyl chloride film and polyester film; laminates of polyurethane film and plyester film; and flexible plastic films on which aluminum has been vapor deposited.

The estradiol percutaneous administration preparations of the present invention may be produced as follows.

First of all, the base is melted under heat, thereafter incorporated with the medicinal substance and crotamiton to form a preparation, after which the thus formed preparation is applied to the above backing material, covered with a liner and then cut into desired pieces to obtain final products; or the thus obtained preparation is once applied to a film which has been treated to have releasability, transferred from the releasable film to a suitable backing material, pressed against the backing material and cut into pieces to obtain final products.

The preparation of the present invention obtained in the above manner enables itself to increase the releasability of the estradiol therefrom, enhance the biological utility and greatly reduce skin stimulus caused thereby in case of continuous or long-term administration thereof.

EXAMPLES

Figure 1:
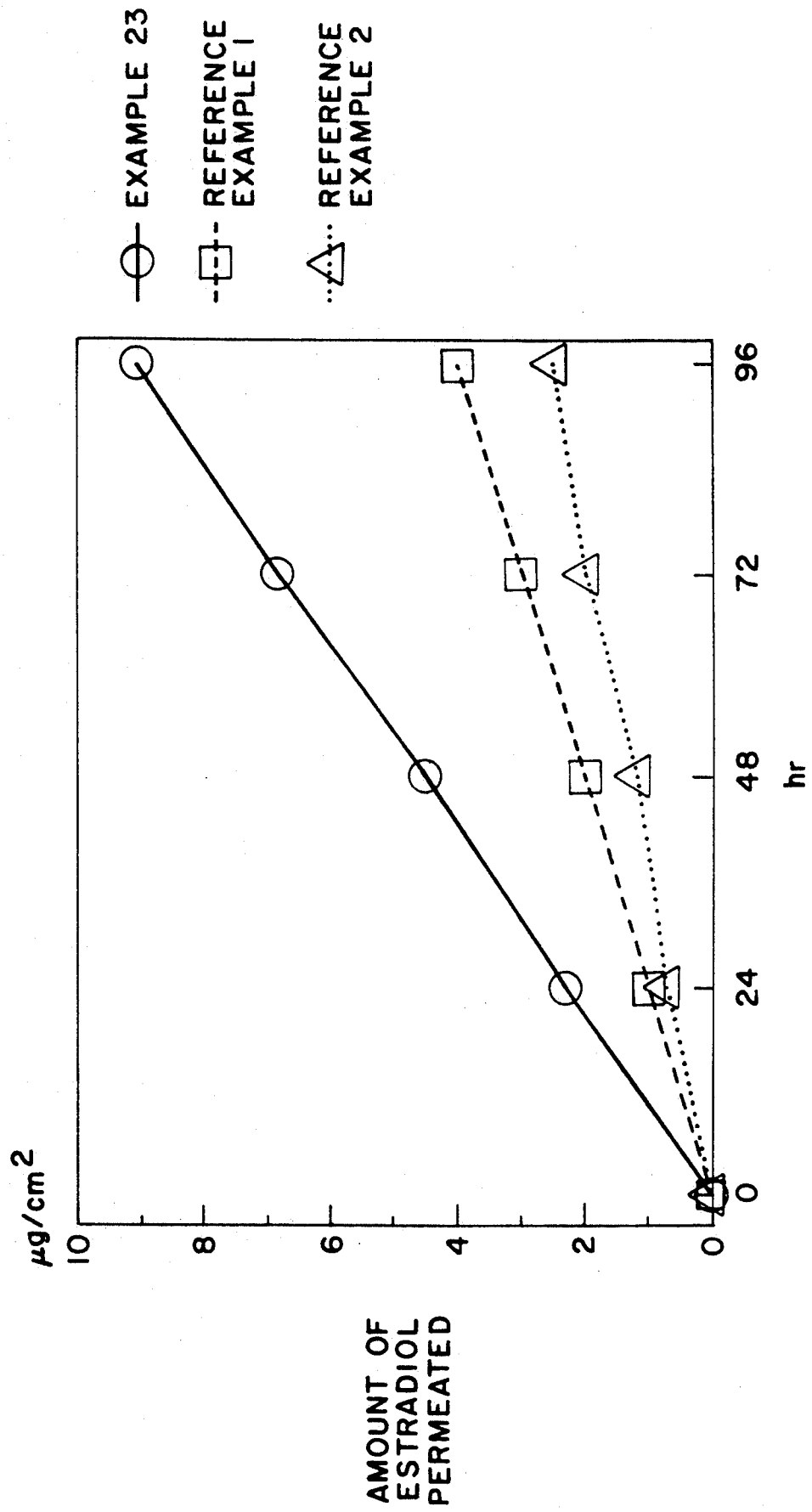
FIG. 1 indicates graphs each showing the amount of estradiol percutaneously permeated with the lapse of time.

The present invention will be better understood by the following Examples, Experiments, Comparative Examples and Reference Examples wherein all the "part" and "parts" are by weight unless otherwise specified.

EXAMPLE 1

| | |
|---|---|
| Styrene-isoprene-styrene block copolymer (Trade name: Califlex TR-1107) | 35.00 parts |
| Liquid paraffin | 56.99 parts |
| Butylhydroxytoluene | 2.00 parts |
| Crotamiton | 1.00 part |
| Super absorbent polymer (Sumikagel SP-520) | 5.00 parts |
| Estradiol | 0.01 part |

In accordance with the above production method, the above ingredients were mixed together, applied to a backing material and then cut into pieces of a desired size to obtain estradiol percutaneous administration matrices.

EXAMPLE 2

| | |
|---|---|
| Styrene-isoprene-styrene block copolymer (Trade name: Califlex TR-1107) | 35.00 parts |
| Liquid paraffin | 52.50 parts |
| Butylhydroxytoluene | 2.00 parts |
| Crotamiton | 5.00 parts |
| Super absorbent polymer (Sumikagel SP-520) | 5.00 parts |
| Estradiol | 0.50 parts |

The procedure of Example 1 was followed except that the above ingredients were used, to obtain estradiol percutaneous administration matrices.

EXAMPLE 3

| | |
|---|---|
| Styrene-isoprene-styrene block copolymer Trade name Califlex TR-1107) | 30.25 parts |
| Liquid paraffin | 32.75 parts |
| Butylhydroxytoluene | 2.00 parts |
| Crotamiton | 20.00 parts |
| Super absorbent polymer (Sumikagel SP-520) | 5.00 parts |
| Estradiol | 10.00 parts |

The procedure of Example 1 was followed except that the above ingredients were used, to obtain estradiol percutaneous administration matrices.

EXAMPLE 4

| | |
|---|---|
| Styrene-isoprene-styrene block copolymer (Trade name: Califlex TR-1107) | 35.00 parts |
| Liquid paraffin | 56.50 parts |
| Butylhydroxytoluene | 2.00 parts |
| Crotamiton | 1.00 part |
| Super absorbent polymer (Trade name: Aquakeep 4SH) | 1.00 part |
| Estradiol | 0.50 parts |

The procedure of Example 1 was followed except that the above ingredients were used, to obtain estradiol percutaneous administration matrices.

EXAMPLE 5

| | |
|---|---|
| Styrene-isoprene-styrene block copolymer (Trade name: Califlex TR-1107 | 20.00 parts |
| Liquid paraffin | 52.50 parts |
| Butylhydroxytoluene | 2.00 parts |
| Crotamiton | 5.00 parts |
| Super absorbent polymer (Trade name: Aquakeep 4SH) | 20.00 parts |
| Estradiol | 0.50 parts |

The procedure of Example 1 was followed except that the above ingredients were used, to obtain estradiol percutaneous administration matrices.

EXAMPLE 6

| | |
|---|---|
| Styrene-isoprene-styrene block copolymer (Trade name: Califlex TR-1107) | 35.00 parts |
| Liquid paraffin | 52.50 parts |
| Butylhydroxytoluene | 2.00 parts |
| Crotamiton | 5.00 parts |
| Super absorbent polymer (Trade name: Arasoap 800F) | 5.00 parts |
| Estradiol | 0.50 parts |

The procedure of Example 1 was followed except that the above ingredients were used, to obtain estradiol percutaneous administration matrices.

EXAMPLE 7

| | |
|---|---|
| Styrene-isoprene-styrene block copolymer (Trade name: Califlex TR-1107 | 35.00 parts |
| Liquid paraffin | 52.50 parts |
| Butylhydroxytoluene | 2.00 parts |
| Crotamiton | 5.00 parts |
| Super absorbent polymer (Trade name: Arasoap S-100F) | 5.00 parts |
| Estradiol | 0.50 parts |

The procedure of Example 1 was followed except that the above ingredients were used, to obtain estradiol percutaneous administration matrices.

EXAMPLE 8

| | |
|---|---|
| Styrene-isoprene-styrene block copolymer (Trade name: Califlex TR-1107) | 35.00 parts |
| Liquid paraffin | 52.50 parts |
| Butylhydroxytoluene | 2.00 parts |
| Crotamiton | 5.00 parts |
| Super absorbent polymer (Trade name: Sanwet IM-300MPS) | 5.00 parts |
| Estradiol | 0.50 parts |

The procedure of Example 1 was followed except that the above ingredients were used, to obtain estradiol percutaneous administration matrices.

EXAMPLE 9

| | |
|---|---|
| Styrene-isoprene-styrene block copolymer (Trade name: Califlex TR-1107) | 35.00 parts |
| Liquid paraffin | 52.50 parts |
| Butylhydroxytoluene | 2.00 parts |
| Crotamiton | 5.00 parts |
| Super absorbent polymer (Trade name: Sanwet IM-1000MPS) | 5.00 parts |
| Estradiol | 0.50 parts |

The procedure of Example 1 was followed except that the above ingredient were used, to obtain estradiol percutaneous administration matrices.

EXAMPLE 10

| | |
|---|---|
| Styrene-isoprene-styrene block copolymer (Trade name: Califlex TR-1107) | 25.00 parts |
| Liquid paraffin | 37.50 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (alicyclic saturated hydrocarbon resin) (Trade name: Arcon P-100) | 25.00 parts |
| Estradiol | 0.50 parts |

The procedure of Example 1 was followed except for the use of the above ingredients, to obtain estradiol percutaneous administration matrices.

EXAMPLE 11

| | |
|---|---|
| Styrene-isoprene-styrene block copolymer (Trade name: Califlex TR-1107) | 5.00 parts |
| Liquid paraffin | 47.50 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (alicyclic saturated hydrocarbon resin) (Trade name: Arcon P-100) | 35.00 parts |
| Estradiol | 0.50 parts |

The procedure of Example 1 was followed except for the use of the above ingredients, to obtain estradiol percutaneous administration matrices.

EXAMPLE 12

| | |
|---|---|
| Styrene-isoprene-styrene block copolymer (Trade name: Califlex TR-1107) | 50.00 parts |
| Liquid paraffin | 25.00 parts |
| Butylhydroxytoluene | 2.00 parts |
| Crotamiton | 5.00 parts |
| Super absorbent polymer (Trade name Sanwet IM-1000MPS) | 5.00 parts |
| Tack-providing agent (alicyclic saturated hydrocarbon resin) (Trade name: Arcon P-100) | 12.50 parts |

| Estradiol | 0.50 parts |

The procedure of Example 1 was followed except for the use of the above ingredients, to obtain estradiol percutaneous administration matrices.

EXAMPLE 13

| | |
|---|---|
| Styrene-isoprene-styrene block copolymer (Trade name: Califlex TR-1107) | 27.00 parts |
| Liquid paraffin | 38.50 parts |
| Butylhydroxytoluene | 2.00 parts |
| Crotamiton | 2.00 parts |
| Super absorbent polymer (Trade name: Sanwet IM-1000MPS) | 5.00 parts |
| Tack-providing agent (rosin ester) (Trade name: KE-311 | 25.00 parts |
| Estradiol | 0.50 parts |

The procedure of Example 1 was followed except for the use of the above ingredients, to obtain estradiol percutaneous administration matrices.

EXAMPLE 14

| | |
|---|---|
| Styrene-isoprene-styrene block copolymer (Trade name: Califlex TR-1107) | 26.50 parts |
| Liquid paraffin | 39.00 parts |
| Butylhydroxytoluene | 2.00 parts |
| Crotamiton | 5.00 parts |
| Super absorbent polymer (Trade name: Sanwet IM-1000MPS) | 2.00 parts |
| Tack-providing agent (rosin ester) (Trade name: KE-311) | 25.00 parts |
| Estradiol | 0.50 parts |

The procedure of Example 1 was followed except for the use of the above ingredients, to obtain estradiol percutaneous administration matrices.

EXAMPLE 15

| | |
|---|---|
| Styrene-isoprene-styrene block copolymer (Trade name: Califlex TR-1107) | 25.00 parts |
| Liquid paraffin | 37.50 parts |
| Butylhydroxytoluene | 2.00 parts |
| Crotamiton | 5.00 parts |
| Super absorbent polymer (Trade name: Sanwet IM-1000MPS | 5.00 parts |
| Tack-providing agent (rosin ester) (Trade name: KE-311) | 25.00 parts |
| Estradiol | 0.50 parts |

The procedure of Example 1 was followed except for the use of the above ingredients, to obtain estradiol percutaneous administration matrices.

EXAMPLE 16

| | |
|---|---|
| Styrene-isoprene-styrene block copolymer (Trade name: Califlex TR-1107) | 22.50 parts |
| Liquid paraffin | 35.00 parts |
| Butylhydroxytoluene | 2.00 parts |
| Crotamiton | 5.00 parts |
| Super absorbent polymer (Trade name: Sanwet IM-1000MPS) | 10.00 parts |
| Tack-providin agent (rosin ester) (Trade name: KE-311) | 25.00 parts |
| Estradiol | 0.50 parts |

The procedure of Example 1 was followed except for the use of the above ingredients, to obtain estradiol percutaneous administration matrices.

EXAMPLE 17

| | |
|---|---|
| Styrene-isoprene-styrene block copolymer (Trade name: Califlex TR-1107) | 22.50 parts |
| Liquid paraffin | 35.00 parts |
| Butylhydroxytoluene | 2.00 parts |
| Crotamiton | 10.00 parts |
| Super absorbent polymer (Trade name: Sanwet IM-1000MPS) | 5.00 parts |
| Tack-providing agent (rosin ester) (Trade name: KE-311) | 25.00 parts |
| Estradiol | 0.50 parts |

The procedure of Example 1 was followed except for the use of the above ingredients, to obtain estradiol percutaneous administration matrices.

EXAMPLE 18

| | |
|---|---|
| Styrene-isoprene-styrene block copolymer (Trade name: Califlex TR-1107) | 25.00 parts |
| Liquid paraffin | 37.50 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (alicyclic saturated hydrocarbon resin) (Trade name: Arcon P-100) | 25.00 parts |
| Estradiol | 0.50 parts |

The procedure of Example 1 was followed except for the use of the above ingredients, to obtain estradiol percutaneous administration matrices.

EXAMPLE 19

| | |
|---|---|
| Styrene-isoprene-styrene block copolymer (Trade name: Califlex TR-1111) | 25.00 parts |
| Liquid paraffin | 37.50 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (alicyclic saturated hydrocarbon resin) (Trade name: Arcon P-100) | 25.00 parts |
| Estradiol | 0.50 parts |

The procedure of Example 1 was followed except for the use of the above ingredients, to obtain estradiol percutaneous administration matrices.

EXAMPLE 20

| | |
|---|---|
| Styrene-isoprene-styrene block copolymer (Trade name: Califlex TR-1107) | 22.50 parts |
| Polyisobutylene | 5.00 parts |
| Liquid paraffin | 35.00 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (alicyclic saturated hydrocarbon resin) (Trade name: Arcon P-100) | 25.00 parts |
| Estradiol | 0.50 parts |

The procedure of Example 1 was followed except for the use of the above ingredients, to obtain estradiol percutaneous administration matrices.

EXAMPLE 21

| | |
|---|---|
| Styrene-isoprene-styrene block copolymer (Trade name: Califlex TR-1111) | 22.50 parts |
| Polyisobutylene | 5.00 parts |
| Liquid paraffin | 35.00 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (alicyclic saturated hydrocarbon resin) (Trade name: Arcon P-100) | 25.00 parts |
| Estradiol | 0.50 parts |

The procedure of Example 1 was followed except for the use of the above ingredients, to obtain estradiol percutaneous administration matrices.

EXAMPLE 22

| | |
|---|---|
| Styrene-isoprene-styrene block copolymer (Trade name: Califlex TR-1111) | 25.00 parts |
| Liquid paraffin | 37.50 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (rosin ester) (Trade name: KE-311) | 25.00 parts |
| Estradiol | 0.50 parts |

The procedure of Example 1 was followed except for the use of the above ingredients, to obtain estradiol percutaneous administration matrices.

EXAMPLE 23

| | |
|---|---|
| Styrene-isoprene-styrene block copolymer (Trade name: Califlex TR-1107) | 22.50 parts |
| Polyisobutylene | 5.00 parts |
| Liquid paraffin | 35.00 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (rosin ester) (Trade name: KE-311) | 25.00 parts |
| Estradiol | 0.50 parts |

The procedure of Example 1 was followed except for the use of the above ingredients, to obtain estradiol percutaneous administration matrices.

EXAMPLE 24

| | |
|---|---|
| Styrene-isoprene-styrene block copolymer (Trade name: Califlex TR-1111) | 22.50 parts |
| Polyisobutylene | 5.00 parts |
| Liquid paraffin | 35.00 parts |
| Butylhydroxytoluene | 2.00 parts |
| Crotamiton | 5.00 parts |
| Super absorbent polymer (Trade name: Sanwet IM-1000MPS) | 5.00 parts |
| Tack-providing agent (rosin ester) (Trade name: KE-311) | 25.00 parts |
| Estradiol | 0.50 parts |

The procedure of Example 1 was followed except that the above ingredients were used, to obtain estradiol percutaneous administration matrices.

COMPARATIVE EXAMPLE 1

| | |
|---|---|
| Styrene-isoprene-styrene block copolymer (Trade name: Califlex TR-1107) | 25.00 parts |
| Polyisobutylene | 5.00 parts |
| Liquid paraffin | 37.50 parts |
| Butylhydroxytoluene | 2.00 parts |
| Crotamiton | 5.00 parts |
| Tack-providing agent (rosin ester) (Trade name: KE-311) | 25.00 parts |
| Estradiol | 0.50 parts |

The procedure of Example 1 was followed except that the above ingredients were used, to obtain estradiol percutaneous administration matrices.

COMPARATIVE EXAMPLE 2

| | |
|---|---|
| Styrene-isoprene-styrene block copolymer (Trade name: Califlex TR-1107) | 25.00 parts |
| Polyisobutylene | 5.00 parts |
| Liquid paraffin | 37.50 parts |
| Butylhydroxytoluene | 2.00 parts |
| Super absorbent polymer (Trade name: Sanwet IM-1000MPS) | 5.00 parts |
| Tack-providing agent (rosin ester) (Trade name: KE-311) | 25.00 parts |
| Estradiol | 0.50 parts |

The procedure of Example 1 was followed except that the above ingredients were used, to obtain estradiol percutaneous administration matrices.

REFERENCE EXAMPLE 1

| | |
|---|---|
| Acryl resin-based solvent-type pressure sensitive adhesive (Trade name: NISSETSU PE-300, solid content 40%) | 95.52 parts |
| (After dried, | 89.53 parts) |
| Crotamiton | 2.13 parts |
| (After dried, | 4.99 parts) |
| Super absorbent polymer (Trade name: Sumikael SP-520) | 2.13 parts |
| (After dried, | 4.99 parts) |
| Estradiol | 0.21 parts |
| (After dried, | 0.49 parts) |

The above ingredients were mixed together to form a mixture which was applied to a backing material in such a manner that the thickness of the thus applied mixture on the backing material was the same as those in the Examples after the solvent of the former has been evaporated. The dried mixture attached to the backing material was cut into pieces of a desired size to obtain estradiol percutaneous administration matrices.

REFERENCE EXAMPLE 2

| | |
|---|---|
| Silicon adhesive (Trade name: Silascon 355 Medical Adhesive) | 89.50 parts |
| Crotamiton | 5.00 parts |
| Super absorbent polymer (Trade name: Sumikagel SP-520) | 5.00 parts |
| Estradiol | 0.50 parts |

The procedure of Reference Example 1 was followed except that the above ingredients were used, to obtain estradiol percutaneous administration matrices.

EXPERIMENT 1

Test for dissolution of estradiol

As indicated hereunder, tests for the dissolution of estradiol were made using solubilizers which are usable in the production (heat melting) of the preparations of the present invention and are indicated in the following Table 1.

Estradiol was mixed with each of the solubilizers in a ratio by weight of from 1 to 2, 4, 8, 12, 16, or 20 to obtain mixtures which were heated at 150° C. for one hour and then maintained at 5° C. for two weeks in order to observe how the estradiol in each of the mixtures was dissolved. The results are shown in Table 1.

TABLE 1

| Ratio of solubilizer to estradiol | x2 | x4 | x8 | x12 | x10 | x20 |
| --- | --- | --- | --- | --- | --- | --- |
| Benzyl alcohol | x | x | x | x | x | x |
| MYL-10 *1 | x | x | x | x | x | x |
| Ethylene glycol | x | x | x | x | x | x |
| Peppermint oil | x | x | x | x | x | x |
| BL-4.2 *2 | x | x | x | x | x | x |
| Crotamiton | x | o | o | o | o | o |
| DIPA *3 | x | x | x | x | x | x |

*1: Surfactant Polyethylenglycol (10) monolaurate
*2: Surfactant Polyoxyethylene (4.2) Lauryl ether
*3: Di-iso-propanolamine In the Table, the mark "O" indicates perfect dissolution and the mark "x" indicates even a slight amount of estradiol crystal remaining undissolved.

It is seen from Table 1 that only crotamiton has excellent solubilizing action.

EXPERIMENT 2

Percutaneous permeation test on hairless mice

Percutaneous permeation tests were made on hairless mice using the preparations obtained in Example 2 and Reference Examples 1-2, respectively. The results are shown in FIG. 1.

As is seen from FIG. 1, the preparation of Example 2 clearly exhibits excellent release of estradiol as compared with those of Reference Examples 1-2. This is because the preparation of the present invention contains the (A−B) nX or (A−B) n−A type elastomer as the base component.

EXPERIMENT 3

Percutaneous permeation test 2 on hairless mice

Figure 2:
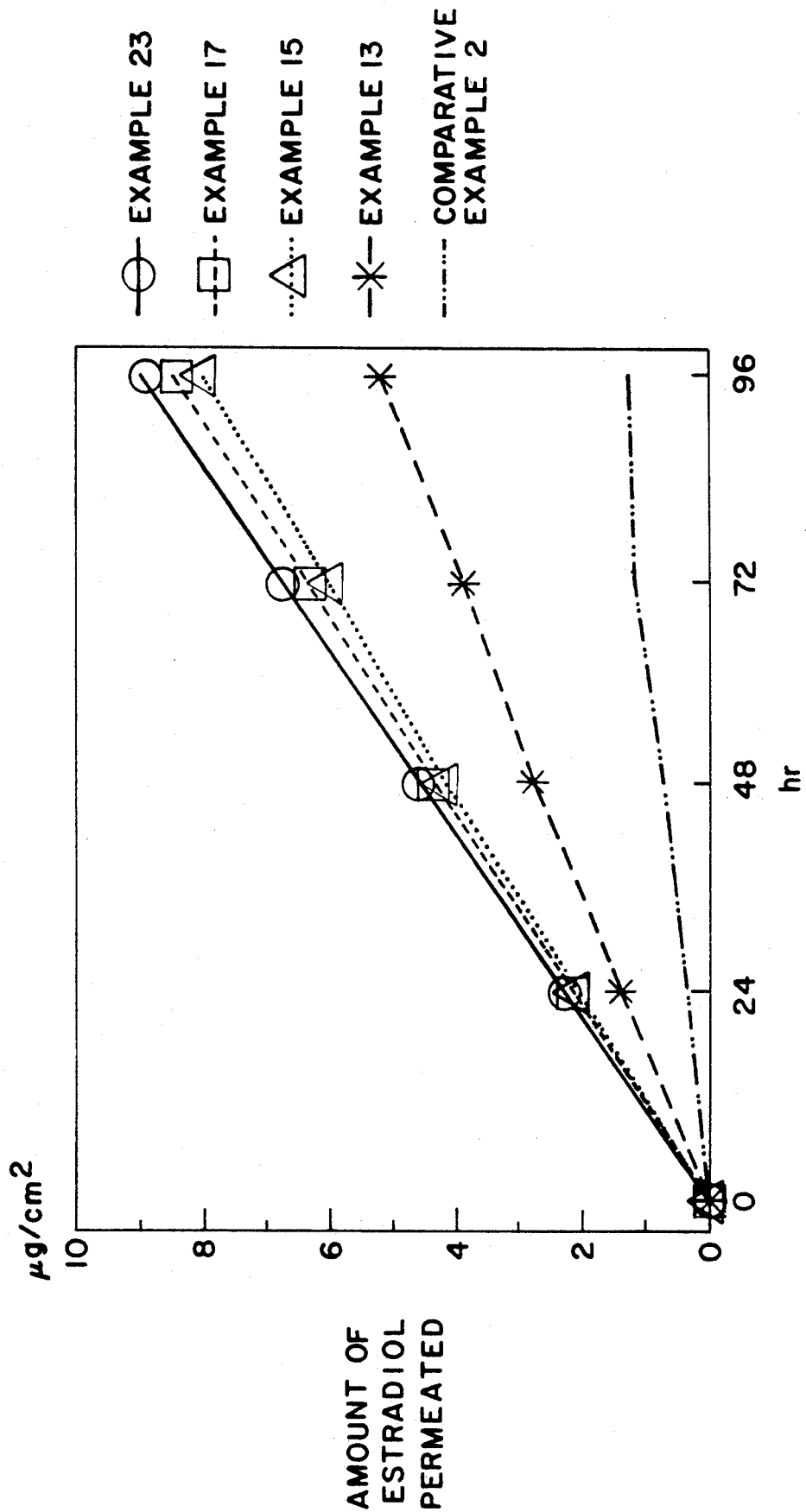
FIG. 2 indicates graphs each showing the amount of estradiol percutaneously permeated with the lapse of time.

Using each of the preparations of Examples 13, 15, 17 and 23, a percutaneous permeation test was made on hairless mice with the results being shown in FIG. 2.

As is shown in FIG. 2, the preparations of Examples 13, 15, 17, and 23 clearly indicate excellent release of estradiol as compared with that of Reference Example 2. This is because the preparation of the present invention contains crotamiton as the absorption accelerator.

EXPERIMENT 4

Skin stimulation test

Using each of the preparations of Examples 14-16, 23 and Comparative Example 1, the preparation was applied to the breast of each of 15 healthy male persons and maintained on the breast for three and a half (3.5) days to observe the condition of the skin with the results being shown in Table 2.

The criteria for estimating the skin stimulation are as follows.

TABLE 2

|  | − | + | ± | ++ | Total | Positivity % above ± |
| --- | --- | --- | --- | --- | --- | --- |
| Example 14 | 13 | 2 | 0 | 0 | 15 | 13.3 |
| Example 15 | 14 | 1 | 0 | 0 | 15 | 6.7 |
| Example 16 | 14 | 1 | 0 | 0 | 15 | 6.7 |
| Example 23 | 14 | 1 | 0 | 0 | 15 | 6.7 |
| Comparative Example 1 | 4 | 3 | 4 | 4 | 15 | 73.3 |

No change: −
Slight rubefaction: ±
Clear rubefaction: +
Serious rash: ++

As is shown in Table 2, the preparations of Examples 14-16 and 23 clearly exhibit less skin stimulation as compared with that of Comparative Example 1, the less skin stimulation being due to the presence of the super absorbent polymercontained in the preparations of the present invention.

EXPERIMENT 5

Test for measuring the estradiol concentration in the blood of rabbits

Using each of the preparations of Examples 13, 15, 17 and 23 as well as the preparation of Comparative Example 2, measurements for estradiol concentration in the blood of rabbits were made. Nippon white-colored hares were depilated in their back and then the estradiol concentrations were measured with the lapse of time with the results being shown in FIG. 3.

Figure 3:
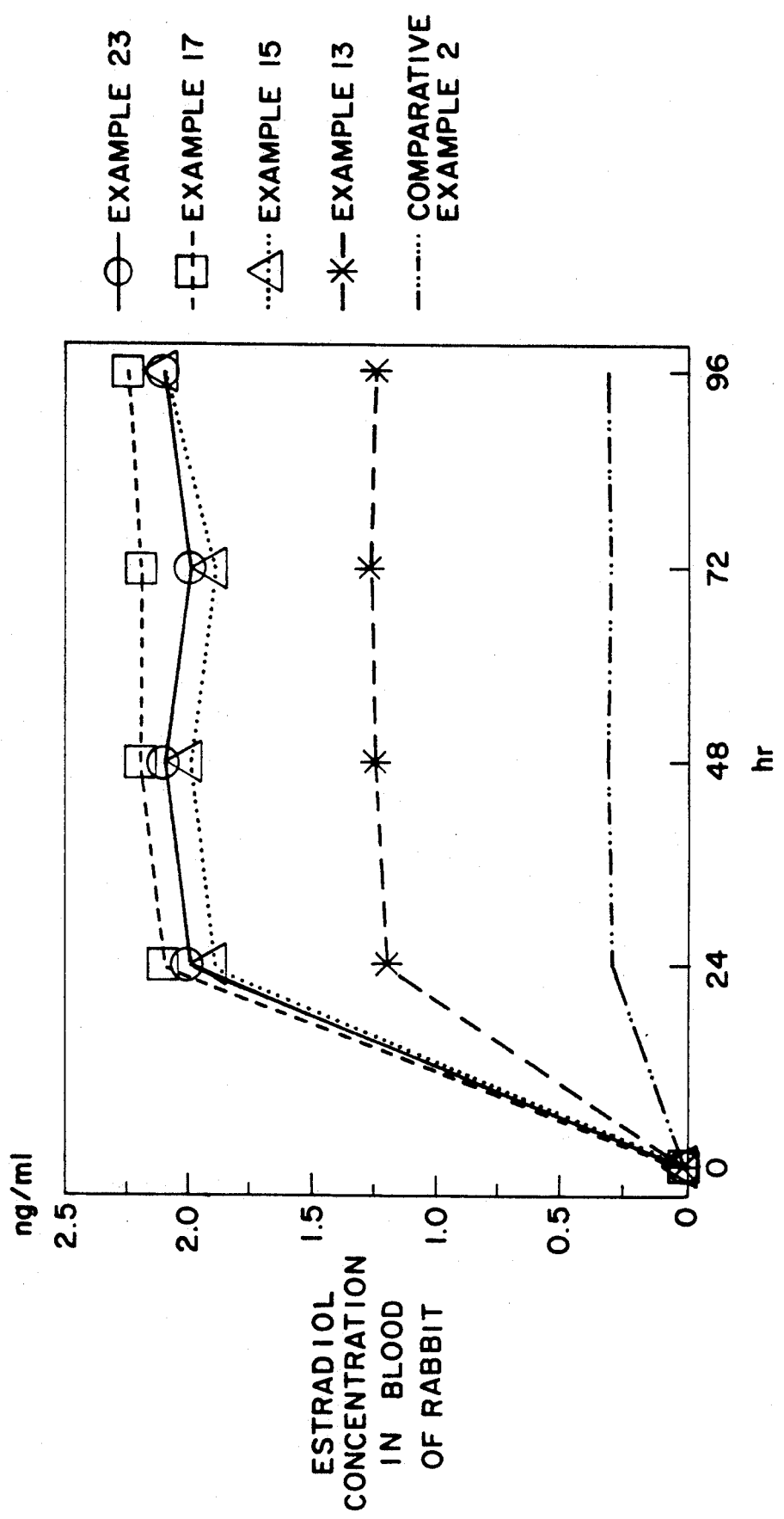
FIG. 3 indicates graphs each showing the concentration of estradiol contained in the blood of a rabbit with the lapse of time.

As is indicated in FIG. 3, the preparations of Examples 13, 15, 17 and 23 are excellent in the rise of concentration of estradiol in blood, the amount of estradiol released and durability as compared with that of Comparative Example 2.

Utilizability in the Industrial Field

The estradiol percutaneous administration preparations of the present invention comprising as essential ingredients the (A−B) nX or (A−B) n−A type elestomer, crotamiton and super absorbent polymer, are most suitable for release of estradiol therefrom, exhibit sufficient medicinal efficacy without causing rubefaction, rashes and the like when used and are industrially very useful as such.

What is claimed is:

1. An estradiol preparation for percutaneous administration comprising the components:
   (1) a styrene-isoprene-styrene block copolymer in the amount of 5-50% by weight;
   (2) crotamiton in the amount of 1-20% by weight;
   (3) a super absorbent polymer in the amount of 1-20% by weight; and
   (4) estradiol in the amount of 0.01-10% by weight.

2. The composition according to claim 1 wherein the total amount of said components (1), (2) and (3) is 30-60% by weight.

3. The composition according to claim 1 which additionally contains at least one member selected from the group consisting of antioxidants, softening agents, tack-providing agents, inorganic fillers, antiaging agents.

4. The composition according to claim 1 which is applied to a backing material which is a member selected from the group consisting of polyester films, polypropylene films, polyethylene films, aluminum foils and flexible laminates thereof, laminates of polyvinyl chloride film and polyester film, laminates of polyurethane films and plyester film, and flexible plastic films on which aluminum has been vapor deposited.

5. The composition according to claim 3 wherein the softening agent is liquid paraffin, the super absorbent polymer is a starch-grafted polyacrylate and the tack-providing agent is a rosin ester.

* * * * *